United States Patent
Deng et al.

(10) Patent No.: US 12,018,335 B2
(45) Date of Patent: Jun. 25, 2024

(54) METHOD FOR QUANTITATIVELY DETECTING DELETION OF HUMAN CDKN2A GENE COPY, PRIMERS AND USE THEREOF

(71) Applicant: Beijing Institute for Cancer Research, Beijing (CN)

(72) Inventors: Dajun Deng, Beijing (CN); Yuan Tian, Beijing (CN); Jing Zhou, Beijing (CN); Zhaojun Liu, Beijing (CN)

(73) Assignee: BEIJING INSTITUTE FOR CANCER RESEARCH, Beijing (CN)

( * ) Notice: Subject to any disclaimer, the term of this patent is extended or adjusted under 35 U.S.C. 154(b) by 0 days.

(21) Appl. No.: 17/611,311

(22) PCT Filed: May 16, 2019

(86) PCT No.: PCT/CN2019/087172
§ 371 (c)(1),
(2) Date: Nov. 15, 2021

(87) PCT Pub. No.: WO2020/228009
PCT Pub. Date: Nov. 19, 2020

(65) Prior Publication Data
US 2022/0275454 A1   Sep. 1, 2022

(51) Int. Cl.
*C12Q 1/6886* (2018.01)
*C12Q 1/6851* (2018.01)

(52) U.S. Cl.
CPC ......... *C12Q 1/6886* (2013.01); *C12Q 1/6851* (2013.01); *C12Q 2600/112* (2013.01); *C12Q 2600/16* (2013.01)

(58) Field of Classification Search
None
See application file for complete search history.

(56) References Cited

U.S. PATENT DOCUMENTS

| 6,773,882 B2* | 8/2004 | Hogan | C12Q 1/6895 |
| | | | 435/6.15 |
| 2011/0136104 A1* | 6/2011 | Pregibon | C12Q 1/6851 |
| | | | 435/6.12 |
| 2013/0059303 A1 | 3/2013 | Radvanyi | |

FOREIGN PATENT DOCUMENTS

| CN | 102517382 A | 6/2012 |
| CN | 103031369 A | 4/2013 |
| CN | 105779465 A | 7/2016 |
| CN | 106609307 A | 5/2017 |
| CN | 106757379 A | 5/2017 |
| CN | 107604062 A | 1/2018 |
| CN | 108315416 A | 7/2018 |
| KR | 20180003919 A | 1/2018 |

OTHER PUBLICATIONS

Gonzalgo et al. (Clinical Cancer Research 1997 vol. 57 p. 5336-5347) (Year: 1997).*
Diffenbach (PCR methods and Applications (1993) vol. 3, pp. S30-S37) (Year: 1993).*
Roux et al (PCR Methods and Applications (1995) vol. 4, pp. s185-s194) (Year: 1995).*
International Search Report of PCT/CN2019/087172.
Written Opinion of PCT/CN2019/087172.
Li, Jin et al., Analysis of p16 Gene Deletion and Mutation in Gastric Carcinoma, Feb. 28, 2007, Acta Academiae Medicinae Jiangxi.
Xie, Huaping et al. Mapping of deletion breakpoints at the CDKN2A locus in melanoma: Detection of MTAP-ANRIL fusion transcripts, Feb. 19, 2016, Oncotarget.

* cited by examiner

*Primary Examiner* — Katherine D Salmon
(74) *Attorney, Agent, or Firm* — Nevrivy Patent Law Group P.L.L.C.

(57) ABSTRACT

Provided are a set of primer pair and probe, having the oligonucleotide sequences as shown in SEQ ID NO: 1, SEQ ID NO: 2 and SEQ ID NO: 3, and a set of primer pair and probe of reference sequence, having the oligonucleotide sequences as shown in SEQ ID NO: 4, SEQ ID NO: 5 and SEQ ID NO: 6. Further provided is the use of the set of primer pair and probe for detecting the common deleted region "chr9:21970277-21985225,hg19", of CDKN2A in the preparation of a kit for quantitatively detecting the deletion of a human CDKN2A gene copy in a DNA sample to be tested. The new method and the specific primer pair and probe can simply, conveniently and specifically detect the deletion of the CDKN2A gene copy in the sample, and have higher sensitivity than conventional detection methods for copy deletion.

5 Claims, 6 Drawing Sheets
Specification includes a Sequence Listing.

ered by reference in the entirety by

SEQUENCE LISTING

```
<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: the  primer  specifically complementary to the
      sequence in the conserved region of common deleted region
      [chr9:21970277-21985225, hg19] of human CDKN2A

<400> SEQUENCE: 1
caggtctgtt tcctcatttg                                                   20

<210> SEQ ID NO 2
<211> LENGTH: 21
<212> TYPE: DNA
<213> ORGANISM: Artificial Sequence
<220> FEATURE:
<223> OTHER INFORMATION: the  primer specifically complementary to the
      sequence in the conserved region of common deleted region
      [chr9:21970277-21985225, hg19] of human CDKN2A

<400> SEQUENCE: 2
ggtcagatta gttgagttgt g                                                 21

<210> SEQ ID NO 3
<211> LENGTH: 20
<212> TYPE: DNA
<213> ORGANISM: Artificial Sequence
<220> FEATURE:
<223> OTHER INFORMATION: the  probe  specifically complementary to the
      sequence in the conserved region of common deleted region
      [chr9:21970277-21985225, hg19] of human CDKN2A

<400> SEQUENCE: 3
ctggctggac caacctcagg                                                   20
```

<210> SEQ ID NO 4
<211> LENGTH: 20
<212> TYPE: DNA
<213> ORGANISM: Artificial Sequence
<220> FEATURE:
<223> OTHER INFORMATION: the primer complementary to the reference
      sequence in the conserved region of GAPDH gene

<400> SEQUENCE: 4
gctcacatat tctggaggag                                              20

<210> SEQ ID NO 5
<211> LENGTH: 20
<212> TYPE: DNA
<213> ORGANISM: Artificial Sequence
<220> FEATURE:
<223> OTHER INFORMATION: the primer complementary to the reference
      sequence in the conserved region of GAPDH gene

<400> SEQUENCE: 5
ggtcattgat ggcaacaata                                              20

<210> SEQ ID NO 6
<211> LENGTH: 23
<212> TYPE: DNA
<213> ORGANISM: Artificial Sequence
<220> FEATURE:
<223> OTHER INFORMATION: the probe complementary to the reference
      sequence in the conserved region of GAPDH gene

<400> SEQUENCE: 6
tgccttcttg cctcttgtct ctt                                          23

<210> SEQ ID NO 7
<211> LENGTH: 20
<212> TYPE: DNA
<213> ORGANISM: Artificial Sequence
<220> FEATURE:
<223> OTHER INFORMATION: the primer designed based on the microsatellite
      D9S1749/ANRIL

<400> SEQUENCE: 7
aggagagggt acgcttgcaa                                              20

<210> SEQ ID NO 8
<211> LENGTH: 22
<212> TYPE: DNA
<213> ORGANISM: Artificial Sequence
<220> FEATURE:
<223> OTHER INFORMATION: the primer designed based on the microsatellite
      D9S1749/ANRIL

<400> SEQUENCE: 8
tacagggtgc gggtgcagat aa                                           22

<210> SEQ ID NO 9
<211> LENGTH: 20
<212> TYPE: DNA
<213> ORGANISM: Artificial Sequence
<220> FEATURE:
<223> OTHER INFORMATION: the primer designed based on the microsatellite
      D9S974/CDKN2A

<400> SEQUENCE: 9
gagcctggtc tggatcataa                                              20

<210> SEQ ID NO 10
<211> LENGTH: 20
<212> TYPE: DNA
<213> ORGANISM: Artificial Sequence
<220> FEATURE:
<223> OTHER INFORMATION: the primer designed based on the microsatellite
      D9S974/CDKN2A

<400> SEQUENCE: 10
aagcttacag aaccagacag                                          20

<210> SEQ ID NO 11
<211> LENGTH: 18
<212> TYPE: DNA
<213> ORGANISM: Artificial Sequence
<220> FEATURE:
<223> OTHER INFORMATION: the primer designed based on the microsatellite
      D9S942/CDKN2A

<400> SEQUENCE: 11
gcaagattcc aaacagta                                            18

<210> SEQ ID NO 12
<211> LENGTH: 20
<212> TYPE: DNA
<213> ORGANISM: Artificial Sequence
<220> FEATURE:
<223> OTHER INFORMATION: the primer designed based on the microsatellite
      D9S942/CDKN2A

<400> SEQUENCE: 12
ctcatcctgc ggaaaccatt                                          20

<210> SEQ ID NO 13
<211> LENGTH: 20
<212> TYPE: DNA
<213> ORGANISM: Artificial Sequence
<220> FEATURE:
<223> OTHER INFORMATION: the primer designed based on the microsatellite
      D9S1748/CDKN2A

<400> SEQUENCE: 13
cacctcagaa gtcagtgagt                                          20

<210> SEQ ID NO 14
<211> LENGTH: 21
<212> TYPE: DNA
<213> ORGANISM: Artificial Sequence
<220> FEATURE:
<223> OTHER INFORMATION: the primer designed based on the microsatellite
      D9S1748/CDKN2A

<400> SEQUENCE: 14
gtgcttgaaa tacaccttc c                                         21

<210> SEQ ID NO 15
<211> LENGTH: 20
<212> TYPE: DNA
<213> ORGANISM: Artificial Sequence
<220> FEATURE:
<223> OTHER INFORMATION: the primer designed based on the microsatellite
      D9S1604/MTAP

<400> SEQUENCE: 15
cctgggtctc caatttgtca                                          20

```
<210> SEQ ID NO 16
<211> LENGTH: 20
<212> TYPE: DNA
<213> ORGANISM: Artificial Sequence
<220> FEATURE:
<223> OTHER INFORMATION: the primer designed based on the microsatellite
      D9S1604/MTAP

<400> SEQUENCE: 16
agcacatgac actgtgtgtg                                                   20

<210> SEQ ID NO 17
<211> LENGTH: 25
<212> TYPE: DNA
<213> ORGANISM: Artificial Sequence
<220> FEATURE:
<223> OTHER INFORMATION: the primer designed based on the microsatellite
      D9S171/FAM186XC3

<400> SEQUENCE: 17
agctaagtga acctcatctc tgtct                                             25

<210> SEQ ID NO 18
<211> LENGTH: 24
<212> TYPE: DNA
<213> ORGANISM: Artificial Sequence
<220> FEATURE:
<223> OTHER INFORMATION: the primer designed based on the microsatellite
      D9S171/FAM186XC3

<400> SEQUENCE: 18
accctagcac tgatggtata gtct                                              24
```

METHOD FOR QUANTITATIVELY DETECTING DELETION OF HUMAN CDKN2A GENE COPY, PRIMERS AND USE THEREOF

CROSS-REFERENCE TO RELATED APPLICATION

This Application is a national stage application of PCT/CN2019/087172. This application claims priority from PCT Application No. PCT/CN2019/087172, filed May 19, 2019, the content of which is incorporated herein in the entirety by reference.

INCORPORATION-BY-REFERENCE OF SEQUENCE LISTING OR TABLE

The material in the accompanying sequence listing is hereby incorporated by reference in its entirety into this application. The accompanying file, named "4_30000_003USN_Replacement_Sequence_Listing.txt" was created on Mar. 21, 2022 and is 4.79 KB.

TECHNICAL FIELD

The present invention relates to the detection field of biotechnology, and more specifically to a method for quantitatively detecting deletion of human CDKN2A gene copy, primers and use thereof.

BACKGROUND ART

The tumor suppressor gene CDKN2A in the short arm of human chromosome 9 encodes both P16 and P14 proteins, which regulate G1 to S phase transition in the cell cycle through P16-CDK4/6-RB and P14-MDM2-P53-P21-RB pathways. The genetic inactivation of this gene is prone to malignant melanoma and pancreatic carcinoma. In the process of tumorigenesis, this gene is mainly inactivated by two ways: somatic copy deletion or abnormal methylation of CpG island, which can be detected in a variety of cancer tissues and precancerous lesion. The gene also is the most frequent gene with large-fragment copy deletion (with average frequency of 8% and >40% in neural tissue tumors; see FIG. 1) in tumor genomes. Inactivation of CDKN2A gene is closely correlated to the risk of canceration of precancerous lesion, the sensitivity of tumor cells to CDK4/6 inhibitors, the efficacy of chemotherapeutic agents, and the overall survival time of tumor patient. It is an important candidate marker of tumor.

Currently, the technology for detecting somatic gene copy variation (SNV) commonly used includes fluorescence-in-situ hybridization (FISH), SNP chip hybridization, microsatellite stability detected using PCR-based single-strand conformation polymorphism (SSCP) or high performance liquid chromatography (HPLC), the first and second generation DNA sequencing technologies and so on. FISH is suitable for detecting gene amplification, but not sensitive for somatic gene copy deletion. SNP chip and microsatellite PCR-SSCP/HPLC assays can be used to detect the deep deletion and amplification of gene copy number for paired tissue samples (for example, including cancerous tissue and the paired normal tissue at surgical margins), with poor sensitivity (minimum detection limit>33%), not suitable for analysis of unpaired single sample. PCR-sequencing method can be used to determine the deletion of gene copy with known deletion site (break/fusion sites), but can't be used to determine long-fragment copy deletion with unknown deletion site. The third generation single DNA molecule real-time sequencing assay can be used for detecting various structural alteration of long-fragment DNA, but it is currently limited to the use of scientific research due to high cost of sequencing.

Although the detection of gene copy amplification has shown good clinical use, the application of somatic gene copy deletion remains blank. Detection technology of gene copy deletion with poor sensitivity can be used for the detection of gene copy deletion of single sample familial/germline and the detection of deletion of paired sample somatic gene copy, but it can't be used for analysis of deletion of somatic gene copy of single sample. Because of the various deletion sites of large gene fragments, even the deletion of CDKN2A gene copy, which is the most frequent gene copy deletion in tumor tissues, for which there is still not sensitive, specific, and convenient assay for detecting single sample (such as biopsy tissue, blood free DNA), which limits its clinical application.

DISCLOSURE OF INVENTION

When we conducted a comprehensive analysis of a large number of previous research documents, we found for the first time that in 84 tumor cell lines or tissue samples having precise coordinates of deletion of CDKN2A gene copy identified by sequencing, there is a 15 kb common deleted sequence (chr9:21,970,277-21,985,225, hg19) between promoter upstream and intron-2 of CDKN2A/P16 gene, although specific coordinates of large-fragment deletion of CDKN2A gene copy are very diverse, see FIG. 2.

Through exploring public somatic copy number variation (SNV) datasets from the cancer genome atlas (TCGA), we also observed approximate distribution of region of deletion of CDKN2A gene copy detected by SNP chip (SNP chip array can't determine precise coordinates of deleted region) also has similar characteristics, see FIG. 3.

Hence, we used microsatellites related to this common deleted sequence as the tested object, and established a method for detecting loss of heterozygosity of CDKN2A common deleted region (CDKN2A-LOH) suitable for comparative analysis of paired samples. After analysis on gastric carcinoma tissues and paired normal control tissues at surgical margins from more than 140 patients suffering from gastric carcinoma, we found that CDKN2A-LOH frequency is significantly and positively correlated with pathological TNM (pTNM) stage of these gastric carcinomas. However, such correlation between pTNM stage of these gastric carcinomas and LOH (nearCDKN2A-LOH) frequency near the CDKN2A common deleted region is not significant. These results reveal that CDKN2A-LOH assay has good clinical application value.

In order to establish a method for detecting the deletion of CDKN2A copy in single sample, we further used the conserved DNA sequence in the common deleted sequence as PCR amplification template, and used the conserved DNA sequence of GAPDH gene without copy mutation in the tumor tissue as the internal reference to design, screen and optimize a set of fluorescence quantitative duplex PCR amplification primers; fluorescence quantitative duplex PCR amplification was performed on the two DNA fragments, and it was found that the number of CDKN2A gene copy is highly stable in genomic DNA of normal people. It is not only suitable for detecting the deletion of CDKN2A copy of paired samples, also suitable for analyzing unpaired single sample, which has not been previously reported.

The present invention provides a set of primer pair and probe, which has the oligonucleotide sequences shown in SEQ ID NO. 1, SEQ ID NO. 2, and SEQ ID NO. 3.

The present invention also provides a set of primer pair and probe for reference sequence, which has the oligonucleotide sequences shown in SEQ ID NO. 4, SEQ ID NO. 5, and SEQ ID NO. 6.

Further, the present invention provides the use of the set of primer pair and probe specifically complementary to the sequence in the conserved region of common deleted region [chr9:21970277-21985225, hg19] of human CDKN2A in the preparation of a reagent or a kit for quantitatively detecting the deletion of human CDKN2A gene copy in DNA sample to be tested. Specifically, the set of primer pair and the probe has the oligonucleotide sequences shown in SEQ ID NO. 1, SEQ ID NO. 2, and SEQ ID NO. 3.

The reagent or the kit of the present invention also includes a set of primer pair and probe complementary to the reference sequence in the conserved region of GAPDH gene, which has the oligonucleotide sequences shown in SEQ ID NO. 4, SEQ ID NO. 5, and SEQ ID NO. 6.

Further, the DNA sample to be tested in the present invention is single sample.

The present invention also provides a method for quantitatively detecting the deletion of human CDKN2A gene copy, comprising following steps:

a. Extract genomic DNA sample of the tissue or the cell to be tested;

b. Extract and prepare DNA standards from the cells with the homozygous deletion of CDKN2A copy and from the cells without the deletion of CDKN2A gene, which have been identified by sequencing, and according to gradient difference, which were continuously diluted as the PCR amplification template of DNA from the cell with the deletion of CDKN2A copy in the proportion of 0% to 100% gradients as to prepare the standard curve;

c. According to the conserved sequence without repetitive sequences, microsatellites, and SNP of frequency>1% in the common deleted region "chr9:21970277-21985225, hg19" of CDKN2A, the primer pair and sequence-specific probe of sample for duplex PCR amplification were designed and synthesized; at the same time, reference primer pair and sequence-specific probe targeted to the reference sequence in the conserved region of the GAPDH gene for duplex PCR amplification were designed and synthesized;

d. Fluorescence quantitative duplex PCR amplification is used to determine the PCR Ct value of each amplified fragment of genomic DNA sequences of the tissue or the cell to be tested and of the reference sequence in the conserved region of GAPDH gene; ΔCt value [CtCDKN2A-CtGAPDH] between the PCR product of common deleted region of CDKN2A and the PCR product of reference sequence was calculated; and the number of CDKN2A copy was calculated according to the standard curve;

e. The number of CDKN2A gene copy in genomic DNA of normal human cells was analyzed, and the range of reference value was established according to mean±1.96×standard deviation (mean±1.96×SD);

f. When the number of CDKN2A gene copy in the tissue or the cell to be tested is lower than the minimum limit of the reference value, it is determined there is the deletion of CDKN2A gene copy in the tissue or the cell to be tested.

Further, the method of the present invention is a method for quantitatively detecting the deletion of human CDKN2A gene copy in single sample, wherein the set of primer pair and sequence-specific probe of sample has the oligonucleotide sequences showed in SEQ ID NO. 1, SEQ ID NO. 2 and SEQ ID NO. 3. The set of primer pair and sequence-specific probe of the reference has the oligonucleotide sequences shown in SEQ ID NO. 4, SEQ ID NO. 5, and SEQ ID NO. 6.

The novel method, the set of specific primer pair and probe of the present invention can easily, conveniently and specifically detect the deletion of CDKN2A gene copy in a sample, and the sensitivity is higher than that by conventional method for detecting copy deletion. This method makes it possible to detect the deletion of CDKN2A gene copy in single sample with unknown coordinates of deletion for the first time, thus the method has application prospect.

In order to better understand the content of the present invention, the content of the present invention will be further described below with reference to accompanying drawings and specific embodiments.

The specific embodiments are only for exemplary purpose and are not intended to limit the present invention in any way.

THE BEST EMBODIMENT TO CARRY OUT THE PRESENT INVENTION

Example 1

Using Conventional Microsatellite Assay to Determine the Loss of Heterozygosity (LOH) of CDKN2A Gene in Paired Gastric Carcinoma Tissues 1. Using conventional phenol-chloroform method to extract DNA from the gastric carcinoma tissue and the normal tissues at its surgical margins after surgical resection (or peripheral white blood cells) from 149 patients;

2. Design of PCR primers: according to the reports in the existing literature, PCR amplification primers of three microsatellites (D9S974, D9S942 and D9S1748, all of which are located between in the first exon α and the first exon β of CDKN2A) closest to the common deleted region of CDKN2A were synthesized; At the same time, PCR amplification primers of three control microsatellites surrounding CDKN2A gene (D9S1604, D9S1749 and D9S171, which are located in MTAP, Anril and FAM186XC3 genes respectively) were synthesized;

| microsatellite/host gene name | PCR primer sequence (5'→3') | Amplified fragment size | PCR annealing temperatures |
|---|---|---|---|
| D9S1749/ANRIL | F: SEQ ID NO. 7<br>R: SEQ ID NO. 8 | 120 bp | 62° C. |
| D9S974/CDKN2A | F: SEQ ID NO. 9<br>R: SEQ ID NO. 10 | 190 bp | 60° C. |
| D9S942/CDKN2A | F: SEQ ID NO. 11<br>R: SEQ ID NO. 12 | 100 bp | 55° C. |
| D9S1748/CDKN2A | F: SEQ ID NO. 13<br>R: SEQ ID NO. 14 | 130 bp | 60° C. |
| D9S1604/MTAP | F: SEQ ID NO. 15<br>R: SEQ ID NO. 16 | 163 bp | 60° C. |
| D9S171/FAM186XC3 | F: SEQ ID NO. 17<br>R: SEQ ID NO. 18 | 158-177 bp | 61° C. |

3. PCR amplification
PCR reaction mixture:

| | |
|---|---|
| Template DNA (20-25 ng) | 1.0 μL |
| 10× Buffer | 2.5 μL |
| dNTP Mix (10 mM each) | 0.5 μL |
| Primer | 0.5 μL |
| HotStar Taq DNA polymerase | 0.2 μL |
| H$_2$O | 20.3 μL |
| Total volume | 25 μL |

Thermal cycle conditions: 95° C., 15 min→[95° C., 30 s→55/60/61/62° C., 30 s→72° C., 30 s] with 34 cycles→72° C., 10 min.

Figure 1:
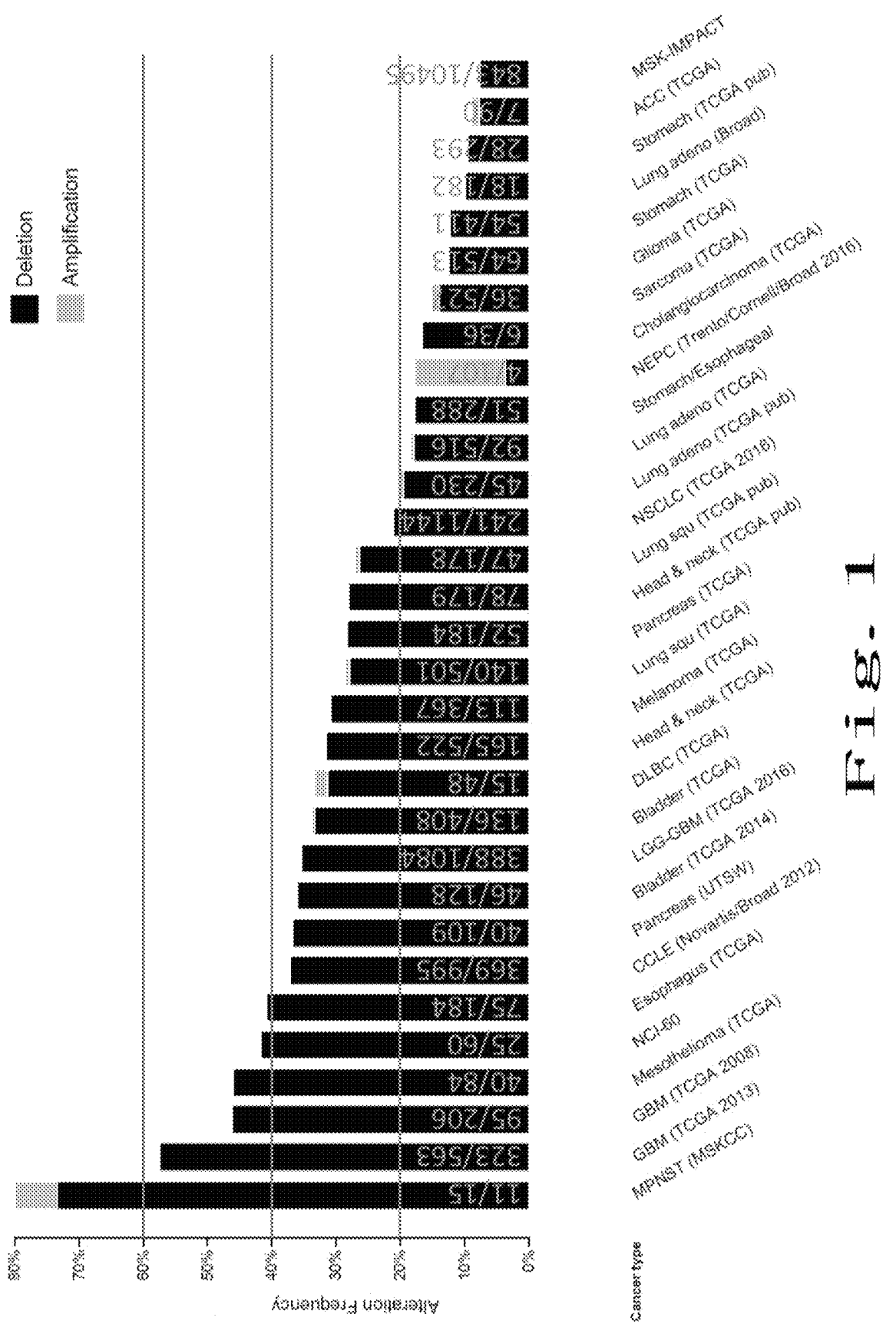
FIG. 1 shows the deep deletion and amplification of CDKN2A gene copy in various tumor tissues/cells made with reference to the public data website of the Human Tumor Genome Project www.cbioportal.org, wherein the gray numbers in various tumors indicate the number of samples with the deep deletion of CDKN2A gene copy/the total number of samples analyzed.
Figure 2:
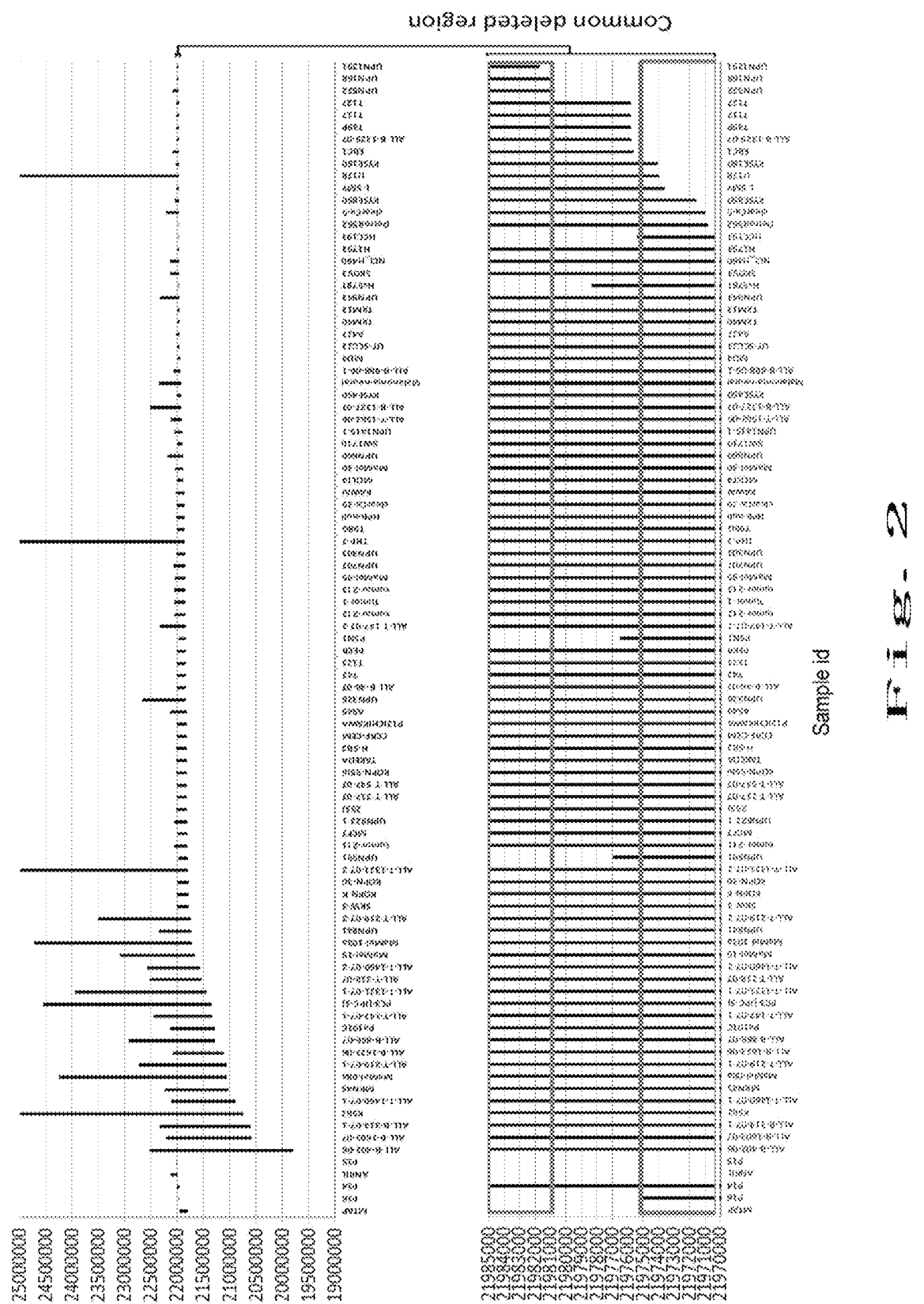
FIG. 2 is the specific location of deleted region of CDKN2A gene copy in the tumor tissue/cell samples (n=84) which has been identified by sequencing [upper figure] and the coordinates of common deleted sequences [chr9: 21970277-21985225, hg19; lower figure] (the coordinates of gene transcription regions of MTAP, P16, P14, ANRIL and P15 are shown on the left side of the figure).
Figure 3:
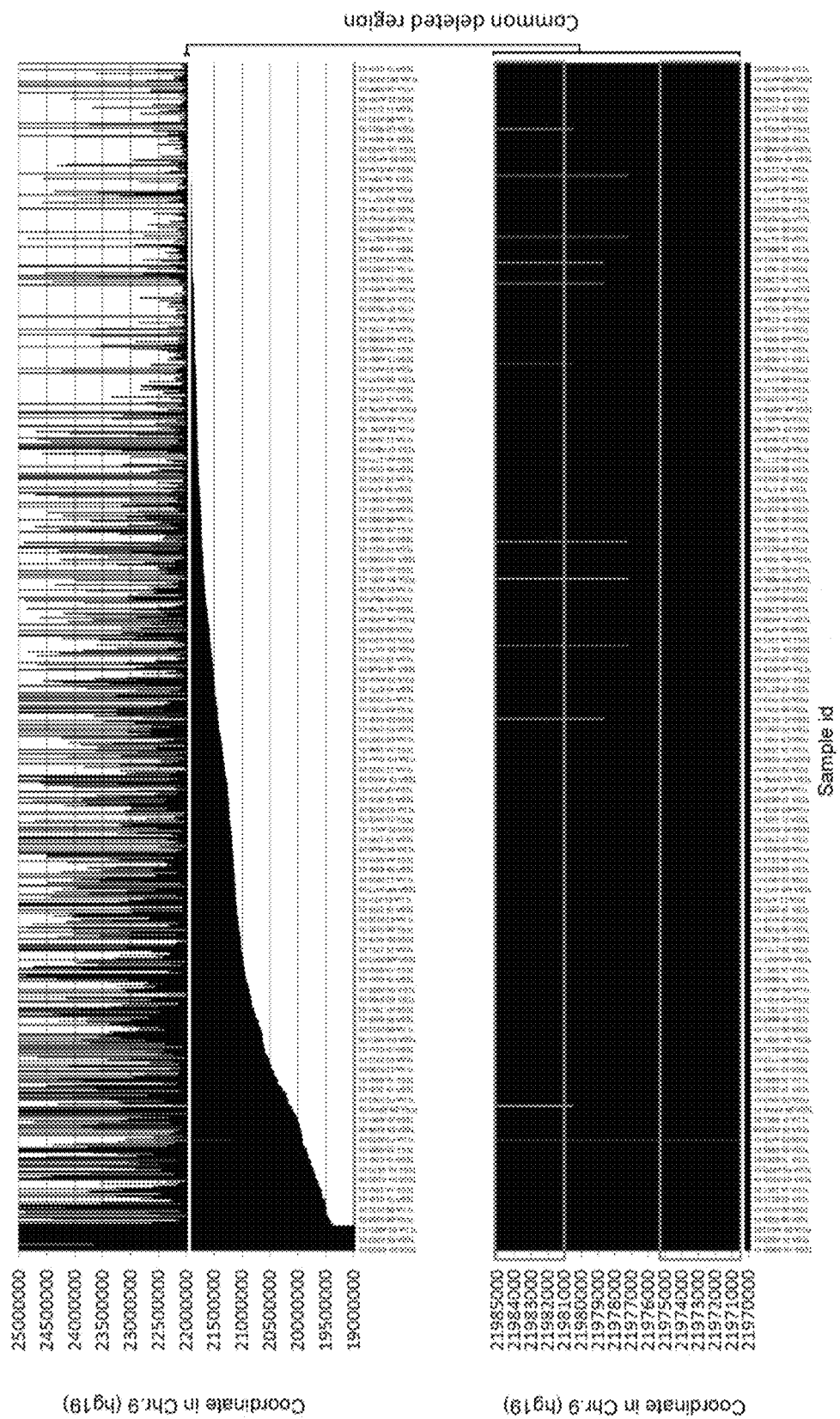
FIG. 3 shows the deleted region [the location in white line; upper figure] and common deleted region [chr9: 21970277-21985225, hg19; lower figure] of CDKN2A gene in tumor tissue samples with the deep deletion of CDKN2A gene copy (n=1187) determined by SNP 6.0 chip (only partial sample markers are shown).
Figure 4:
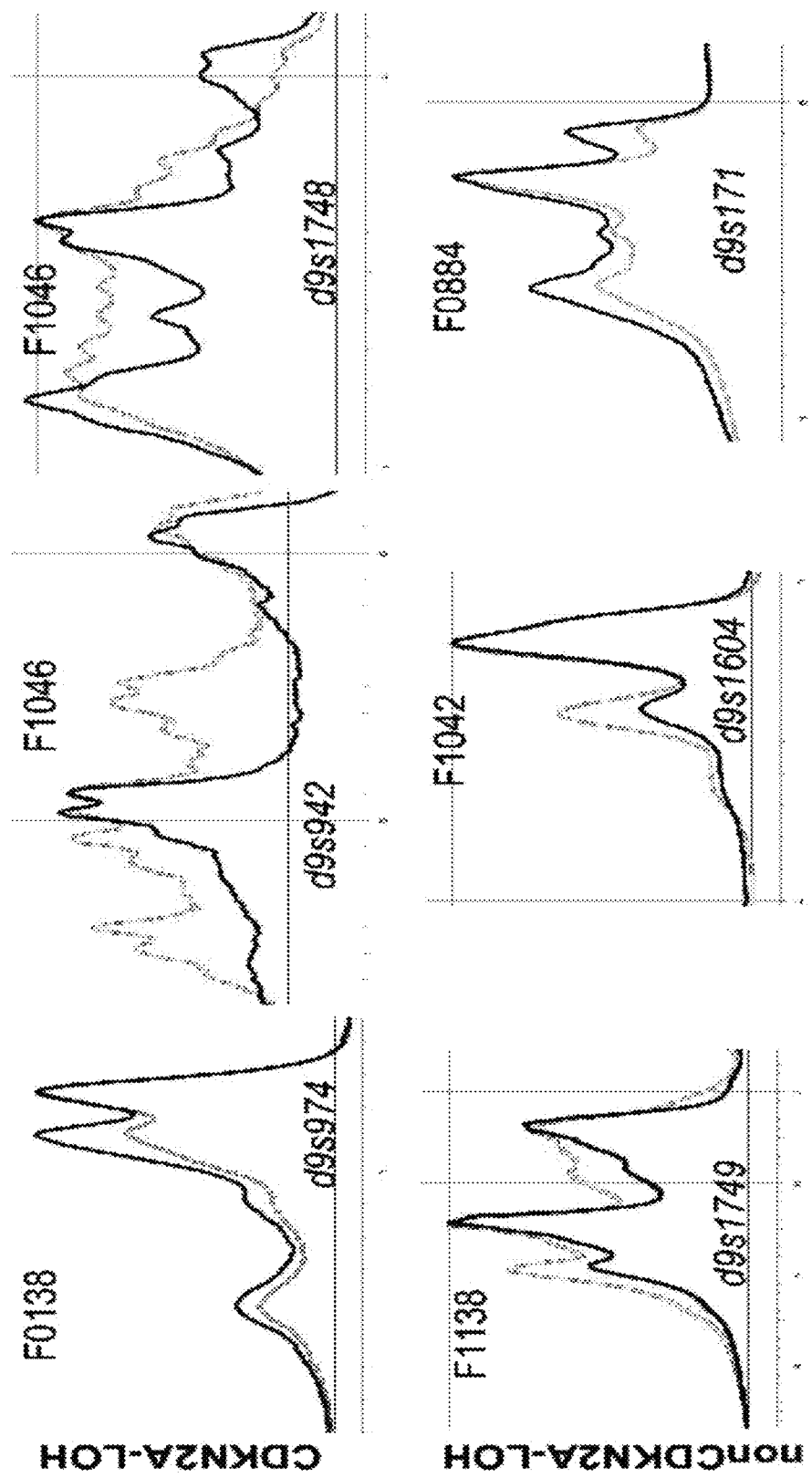
FIG. 4 is a representative DHPLC chromatogram of instability of 6 microsatellites at the site 9p21 in gastric carcinoma genome, where the black line represents gastric carcinoma tissue and the gray line represents normal tissue.

4. The PCR products were separated and determined by the molecular size of products by DHPLC, and the results are shown in FIG. 4.

5. Determination of the microsatellite instability of sample:
(1) determination criteria: compared with the chromatogram of normal tissue, when partial chromatographic peaks in tumor tissue disappear completely or the the ratio of peak height decreases by more than 50%, or the shape or number of chromatographic peaks change significantly, it was determined that there was this microsatellite instability (MSI);
(2) When there was MSI in any one of the three microsatellites (D9S974, D9S942, D9S1748) related to the common deleted region of CDKN2A, it was determined that there was a loss of heterozygosity in the common deleted region of CDKN2A (CDKN2A-LOH);
(3) When there was MSI in any one of the peripheral three microsatellites (D9S1604, D9S1749, D9S171) of the CDKN2A gene, it was determined that there was a loss of heterozygosity in the peripheral region of CDKN2A gene (nearCDKN2A-LOH);

6. Comparison of clinical significances of CDKN2A-LOH and nearCDKN2A-LOH
(1) CDKN2A-LOH was detected in 52 gastric carcinoma samples, and nearCDKN2A-LOH was detected in 41 gastric carcinoma samples; among them, both CDKN2A-LOH and nearCDKN2A-LOH were detected in 31 samples;
(2) The detection of CDKN2A-LOH was significantly correlated with pTNM stage of gastric carcinomas: 24.0% (12/50) for stage-I, 33.3% (14/42) for stage-III, 45.6% (26/57) for stage-IV, and the difference is statistically significant (Trend test, p<0.02, two-sided). Although the detection of nearCDKN2A-LOH was also correlated with pTNM stage of gastric carcinomas: 22.0% (11/50) for stage-I, 28.6% (12/42) for stage-III, 31.6% (18/57) for stage-IV, the difference is not statistically significant (Trend test, p=0.55);
6. Conclusion: although the above 6 microsatellites are commonly used to detect the site LOH at chromosome 9p21, compared with the MSI of peripheral three control microsatellites (D9S1604, D9S1749, D9S171) of common deleted region of CDKN2A, the MSI of three microsatellites (D9S974, D9S942, D9S1748) near the common deleted region of CDKN2A was used to detect site LOH at chromosome 9p21, which was more valuable for prognostic determination of gastric carcinomas. It also further confirmed good application prospect of detecting the common deleted region of CDKN2A.

Example 2

The Detection of Deletion of CDKN2A Gene Copy in Gastric Carcinoma Tissue by Fluorescence Quantitative Duplex PCR Assay 1. Using conventional phenol-chloroform method to extract DNA from the gastric carcinoma tissue and the normal tissues at its surgical margins after surgical resection from 140 patients;
2. Preparing a mixture of A549 cells with homozygous deletion in the common deleted region of CDKN2A and RKO cells without deletion, so that the proportion of A549 cell DNA is 100%, 90%, 80%, 70%, 60%, 50%, 40%, 30%, 20%, 10% and 0, respectively;
3. Primers and fluorescent labeled probes for multiplex PCR amplification of the conserved sequence of the second intron in the common deleted region of CDKN2A were synthesized. The oligonucleotide sequences thereof are shown in SEQ ID No.1, SEQ ID No.2 and SEQ ID No.3 Primers and fluorescent labeled probes for multiplex PCR amplification of the conserved sequence of GAPDH gene were synthesized. The oligonucleotide sequences thereof are shown in SEQ ID No.4, SEQ ID No.5 and SEQ ID No.6;

| Amplicon | Primer ID | Primer and probe (5'-3') | Product size |
|---|---|---|---|
| intron2/CDKN2A | 1 | P16-F: SEQ ID NO. 1 | 129 bp |
| | 2 | P16-R: SEQ ID NO. 2 | |
| | 3 | P16-Probe: FAM-SEQ ID NO. 3-BHQ1 | |

-continued

| Amplicon | Primer ID | Primer and probe (5'-3') | Product size |
|---|---|---|---|
| Reference/GAPDH | 4 | GAPDH-F: SEQ ID NO. 4 | 135 bp |
|  | 5 | GAPDH-R: SEQ ID NO. 5 |  |
|  | 6 | GAPDH-Probe: Cy5-SEQ ID NO. 6-BHQ2 |  |

4. Prepare PCR reaction mixture:

| | |
|---|---|
| Sample DNA (20-25 ng) | 2.0 μL |
| TaqMan Universal Master Mix II | 10.0 μL |
| Multiplex Primer mix (50 μM for each) | 2.0 μL |
| Probes (50 μM for each) | 2.0 μL |
| H$_2$O | 7.2 μL |
| Total volume | 20 μL (/PCR tube) |

Figure 5:
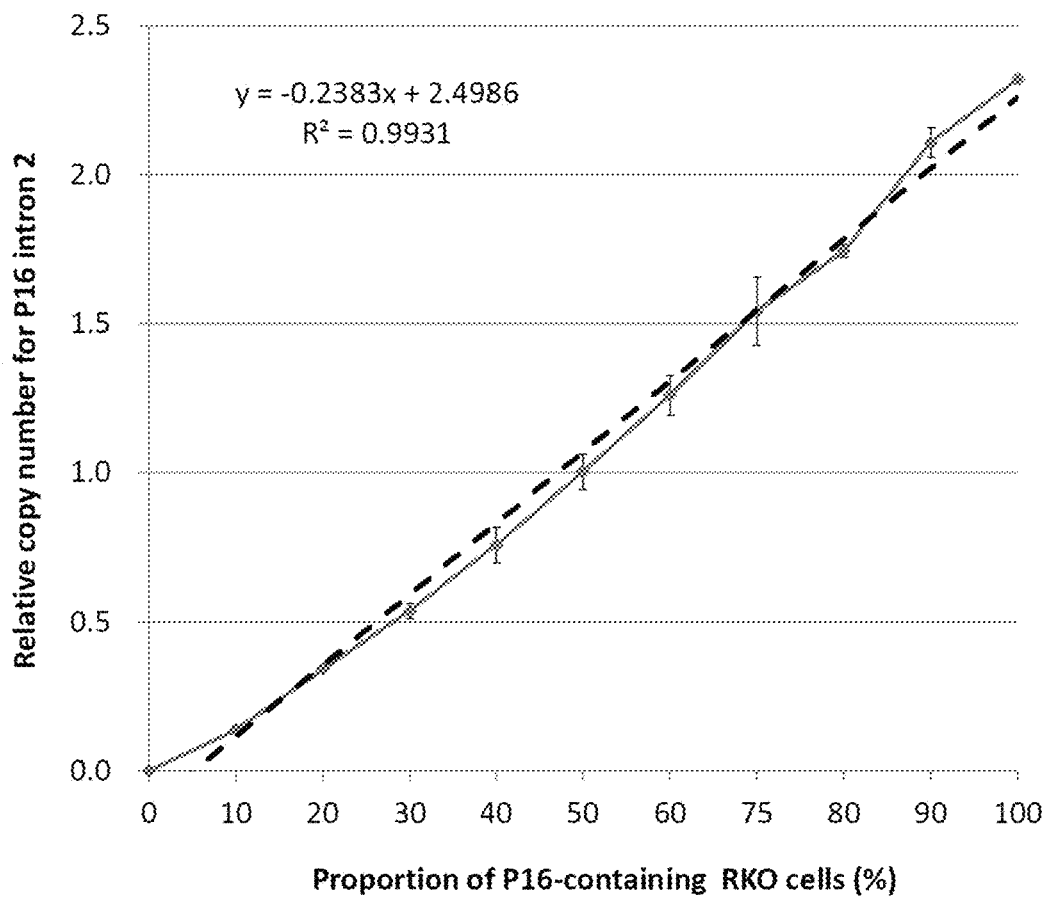
FIG. 5 is a standard curve of deletion of P16 gene copy determined by fluorescence quantitative duplex PCR assay.
Figure 6:
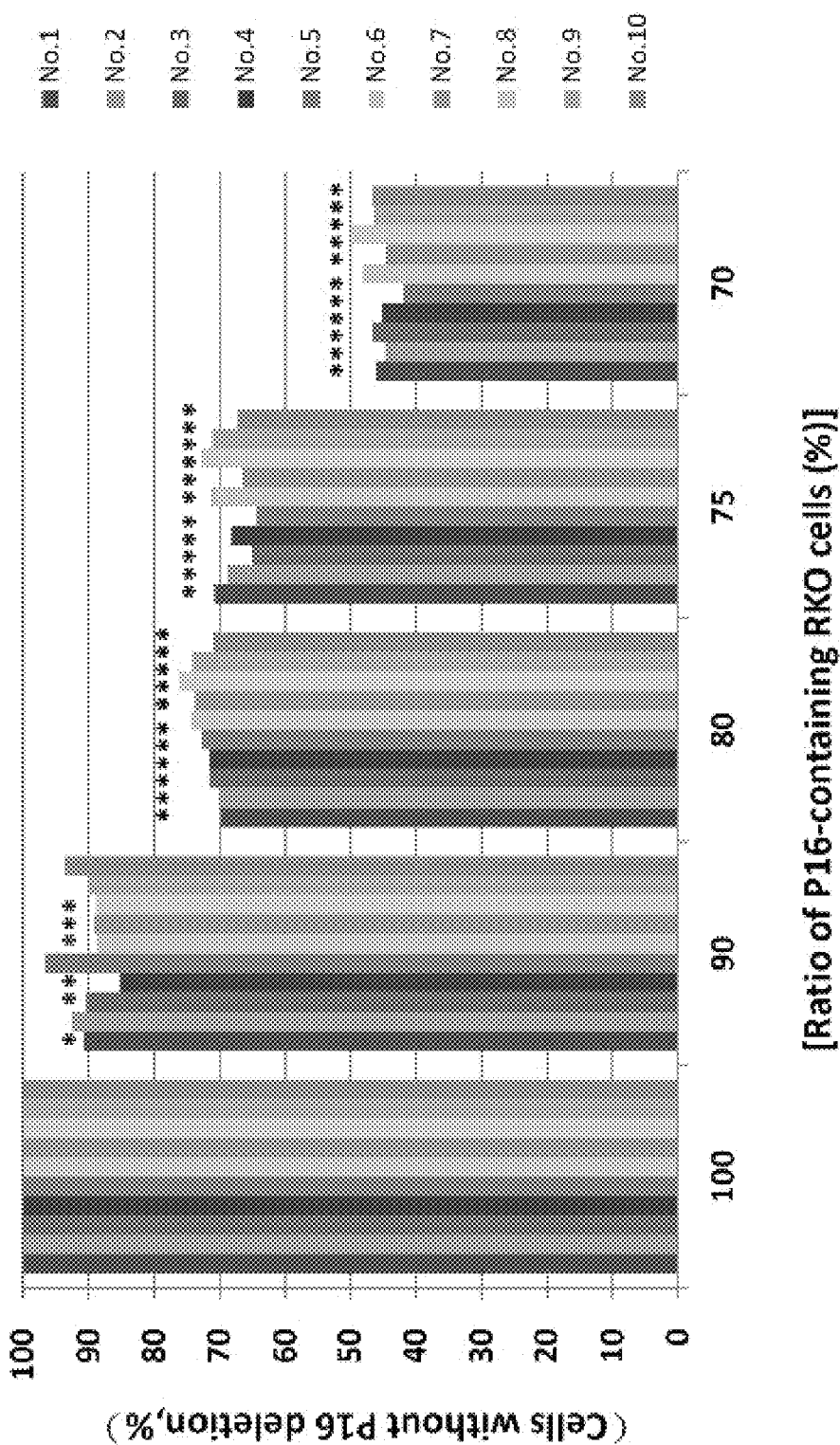
FIG. 6 shows the reproducibility of deletion of p16 gene copy determined by fluorescence quantitative duplex PCR assay in the presence of different RKO cell ratios without p16 deletion (daily repeat experiment).

5. Three parallel PCR tubes were set for each sample and the amplification was performed on a multi-channel real-time quantitative PCR instrument. Thermal cycle conditions: denaturing at 95° C. for 10 minutes→[denaturing at 95° C. for 15 seconds→annealing at 60° C. for 1 minute] with 40 cycles; the Ct values of the amplified fragments of reference sequence and the sequence to be tested were read at the anneal step for each cycle; the difference value (ΔCt value) between the Ct values of the target sequence and the reference sequence in each PCR tube as well as the relative copy number of CDKN2A gene were calculated;

6. A549 cell DNA with the deletion of P16 gene copy was used to dilute equal concentration of RKO cell DNA without the deletion of P16 gene copy. The standard curve was formulated according to the relative copy number of A549 cell DNA with the deletion of CDKN2A gene with different dilution concentrations, thus the linear range of copy deletion of CDKN2A gene determined by this method was calculated as 100%-10%, see FIG. 5;

7. Setting of minimum detection limit: although the average copy number of CDKN2A gene in 10% A549 cells (including 90% RKO cells) was always lower than that in control RKO cell, there is P>0.05 in four of ten repeated experiments. The average copy number of CDKN2A gene in 20% or higher concentration of A549 cells was always lower than that in control RKO cell, and the p value was always<0.05. Therefore, the minimum detection limit of this method should be 20%, see FIG. 6;

8. Paired samples were compared and analyzed to determine positive results of deletion of CDKN2A gene copy: when the number of CDKN2A gene copy of the sample to be tested was 20% lower than that of the normal control sample, and the difference was statistically significant (P<0.05), it was determined that the deletion of CDKN2A gene copy was positive in the sample.

9. Results
   (1) Among the gastric carcinoma tissues from 140 patients suffering from the gastric carcinoma, the deletion of p16 gene copy was positive in 37 cases (26.4%); In gastric carcinoma tissues with positive vascular cancer embolus and its distant metastasis, the positive rate of deletion of CDKN2A gene copy was significantly higher than that gastric carcinoma tissues without vascular cancer embolus and its distant metastasis;
   (2) the positive detection rate of deletion of CDKN2A gene copy was highly correlated with pTNM stage of gastric carcinoma: 17.0% (8/47) for stage-I, 23.1% (9/39) for stage-III and 37.0% (20/54) for stage-IV, and the difference was statistically significant (trend test, p<0.02, two-sided; table 1).

TABLE 1

Analysis of the correlation between deletion of p16 gene copy and clinicopathological characteristics in gastric carcinoma tissue

| | | P16 deletion (paired sample comparison) | | | | P16 deletion (single sample analysis) | | | |
|---|---|---|---|---|---|---|---|---|---|
| | | Positive | Negative | Ratio(%) | p-value | Positive | Negative | Ratio(%) | p-value |
| Sex | Male | 18 | 76 | 19.1 | | 34 | 70 | 32.7 | |
| | Female | 9 | 27 | 25.0 | | 7 | 29 | 19.4 | |
| Differentiation | Poor | 23 | 79 | 22.5 | | 23 | 79 | 22.5 | 0.004 |
| | Mod& Well | 14 | 24 | 36.8 | | 18 | 20 | 47.4 | |
| Vessel embolus | Positive | 26 | 53 | 32.9 | 0.048 | 29 | 50 | 36.7 | 0.028 |
| | Negative | 11 | 50 | 18.0 | | 12 | 49 | 19.7 | |
| pTNM stage | I | 8 | 39 | 17.0 | 0.020 | 10 | 37 | 21.3 | |
| | III | 9 | 30 | 23.1 | | 12 | 27 | 30.8 | |
| | IV | 20 | 34 | 37.0 | | 19 | 35 | 35.2 | |
| Invasion | 1 | 7 | 18 | 28.0 | | 10 | 15 | 40.0 | |
| | 3&4 | 30 | 85 | 26.1 | | 31 | 84 | 27.0 | |
| Distant_metastasis | Positive | 15 | 18 | 45.5 | 0.005 | 14 | 19 | 42.4 | 0.058 |
| | Negative | 22 | 85 | 20.6 | | 27 | 80 | 25.2 | |
| Node_metastasis | Positive | 25 | 65 | 27.8 | | 29 | 61 | 32.2 | |
| | Negative | 12 | 38 | 24.0 | | 12 | 38 | 24.0 | |
| Total | | 37 | 103 | 26.4 | | 41 | 99 | 29.3 | |

10. The determination of positive results of deletion of CDKN2A gene copy by single sample analysis: the average value of relative copy number of CDKN2A gene in normal paired tissues of gastric mucosa without carcinoma from 140 patients suffering from gastric carcinoma was 3.27 (100%), and the standard deviation was 0.26. The reference value of 1.96 standard deviations floating up and down was 2.75~3.79. When the relative copy number of CDKN2A gene of the sample to be tested was lower than the minimum limit 2.75 of reference value, it was determined that the deletion of CDKN2A gene copy was positive.

11. Results (1) Using the minimum limit 2.75 of reference value of as the standard, the deletion of CDKN2A gene copy in gastric carcinoma tissues was detected and determined. the deletion of CDKN2A gene copy was positive in 41 gastric carcinoma samples. Among them, 32 samples were those that were determined as positive for the deletion of CDKN2A gene copy in paired comparison, and 10 samples were those that were determined as negative for copy deletion of CDKN2A gene in paired comparison. If the result of paired comparison was used as gold standard, the sensitivity of the single-sample method is 86.5% (32/37), and the specificity is 91.3% (94/103);

(2) The analysis of clinicopathological characteristics shows that in gastric carcinoma tissues with positive vascular cancer embolus and its distant metastasis, the positive rate of deletion of CDKN2A gene copy detected by single-sample analysis was significantly higher than that in gastric carcinoma tissues with negative vascular cancer embolus and without distant metastasis, see Table 1;

12. Conclusion

This method is not only suitable for analysis of the deletion of CDKN2A/P16 gene copy in paired samples, but also for single sample.

INDUSTRIAL APPLICABILITY

The inventors of the present invention discovered the common deleted region of human CDKN2A "chr9: 21970277-21985225, hg19", and thus designed a set of specific primer pair and probe complementary to the conserved region of the common deletion region, and analyzed the deletion of CDKN2A/p16 gene copy of a single sample with high sensitivity of 86.5% (32/37) and specificity of 91.3% (94/103).

Because it has been confirmed in existing studies that the deletion of human CDKN2A gene copy is significantly related to the incidence, metastasis and prognosis of many cancers, the set of primer pair and probe of the present invention for detecting the common deleted region of human CDKN2A "chr9: 21970277-21985225, hg19" can be used to prepare a reagent or a kit for quantitatively detecting the deletion of human CDKN2A gene copy in DNA samples to be tested for estimating the incidence, metastasis and prognosis of cancer.

Example 2 of the present invention is only an exemplary embodiment, and the average value and the standard deviation mentioned therein can be finally determined by those skilled in the art according to the method provided by the present invention and cancer types.

The invention claimed is:

1. A set of an oligonucleotide primer pair and fluorescently labeled oligonucleotide probe, wherein the oligonucleotide primer pair comprises a first oligonucleotide comprising SEQ ID NO: 1 and a second oligonucleotide comprising SEQ ID NO:2, and the fluorescently labeled oligonucleotide probe comprises SEQ ID NO:3.

2. The set of an oligonucleotide primer pair and fluorescently labeled oligonucleotide probe of claim 1, wherein the fluorescently labeled oligonucleotide probe comprises a fluorophore located at the 5' end of the probe.

3. The set of an oligonucleotide primer pair and fluorescently labeled oligonucleotide probe of claim 2, wherein the fluorophore is fluorescein (FAM).

4. The set of an oligonucleotide primer pair and fluorescently labeled oligonucleotide probe of claim 3, wherein the fluorescently labeled oligonucleotide probe comprises a quencher located at the 3' end of the probe.

5. The set of an oligonucleotide primer pair and fluorescently labeled oligonucleotide probe of claim 4, wherein the quencher is BHQ1.

* * * * *